(12) United States Patent
Wolkers et al.

(10) Patent No.: US 6,723,497 B2
(45) Date of Patent: Apr. 20, 2004

(54) THERAPEUTIC PLATELETS AND METHODS

(75) Inventors: Willem F. Wolkers, Davis, CA (US); John H. Crowe, Davis, CA (US); Fern Tablin, Davis, CA (US); Ann E. Oliver, Davis, CA (US); Naomi J. Walker, Davis, CA (US); Nelly Tsvetkova, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 65 days.

(21) Appl. No.: 09/828,627

(22) Filed: Apr. 5, 2001

(65) Prior Publication Data

US 2001/0019819 A1 Sep. 6, 2001

Related U.S. Application Data

(63) Continuation of application No. 09/501,773, filed on Feb. 10, 2000, now abandoned.

(51) Int. Cl.⁷ ................................................. C12N 5/00
(52) U.S. Cl. .............................. 435/2; 435/374; 436/18; 424/532; 536/123.13
(58) Field of Search ....................... 435/2, 374; 436/18; 424/532; 536/123.13

(56) References Cited

U.S. PATENT DOCUMENTS

| | | |
|---|---|---|
| 3,932,943 A | 1/1976 | Briggs et al. |
| 4,145,185 A | 3/1979 | Brinkhous et al. |
| 4,251,995 A | 2/1981 | Pert et al. |
| 4,287,087 A | 9/1981 | Brinkhous et al. |
| 4,302,355 A | 11/1981 | Turner, Jr. et al. |
| 4,585,735 A | 4/1986 | Meryman et al. |
| 4,695,460 A | 9/1987 | Holme |
| 4,717,654 A | 1/1988 | Savoca et al. |
| 4,874,690 A | 10/1989 | Goodrich et al. |
| 4,880,788 A | 11/1989 | Moake et al. |
| 4,891,319 A | 1/1990 | Roser |
| 4,994,367 A | 2/1991 | Bode et al. |
| 5,026,566 A | 6/1991 | Roser |
| 5,030,560 A | 7/1991 | Sinor et al. |
| 5,043,261 A | 8/1991 | Goodrich et al. |
| 5,045,446 A | 9/1991 | Goodrich, Jr. et al. |
| 5,059,518 A | 10/1991 | Kortright et al. |
| 5,149,653 A | 9/1992 | Roser |
| 5,151,360 A | 9/1992 | Handa et al. |
| 5,153,004 A | 10/1992 | Goodrich, Jr. et al. |
| 5,165,938 A | 11/1992 | Knighton |
| 5,171,661 A | 12/1992 | Goodrich, Jr. et al. |
| 5,178,884 A | 1/1993 | Goodrich et al. |
| 5,213,814 A | 5/1993 | Goodrich, Jr. et al. |
| 5,236,716 A | 8/1993 | Carmen et al. |
| 5,242,792 A | 9/1993 | Rudolph et al. |
| 5,248,506 A | 9/1993 | Holme et al. |
| 5,250,303 A | 10/1993 | Meryman et al. |
| 5,328,840 A | 7/1994 | Coller |
| 5,332,578 A | 7/1994 | Chao |
| 5,344,752 A | 9/1994 | Murphy |
| 5,358,844 A | 10/1994 | Stossel et al. |
| 5,376,524 A | 12/1994 | Murphy et al. |
| 5,378,601 A | 1/1995 | Gepner-Puszkin |
| 5,428,008 A | 6/1995 | Chao et al. |
| 5,510,263 A | 4/1996 | Quaranta et al. |
| 5,651,966 A | 7/1997 | Read et al. |
| 5,736,313 A | 4/1998 | Spargo et al. |
| 5,759,542 A | 6/1998 | Gurewich |
| 5,827,741 A | 10/1998 | Beattie et al. |
| 5,902,608 A | 5/1999 | Read et al. |
| 5,958,670 A | 9/1999 | Goodrich, Jr. et al. |
| 6,221,575 B1 | 4/2001 | Roser et al. |

FOREIGN PATENT DOCUMENTS

| | | |
|---|---|---|
| EP | 0356257 A2 | 2/1990 |
| EP | 0356257 B1 | 3/1995 |
| EP | 0668013 A2 | 8/1995 |
| WO | WO 86/03938 | 7/1986 |
| WO | WO 87/05300 | 9/1987 |
| WO | WO 90/04329 | 5/1990 |
| WO | WO 93/00806 | 1/1993 |
| WO | WO 93/14191 | 7/1993 |
| WO | WO 01/30141 A1 | 5/2001 |

OTHER PUBLICATIONS

E.A.J. Bateson et al., "Electrokinetic Properties of Human Cryopreserved Platelets", proceeds from Clinical Chemistry Department, Guy's Hospital, London: Department of Cell Biology and Biochemistry, Hunterian Institute, Royal College of Surgeons, pp. 213–291, 1994.

Kenneth Hughes and Neville Crawford, "Reversibly Electropermeabilized Platelets: Potential Use as Vehicles for Drug Delivery", Department of Biochemistry, Hunterian Institute, Royal College of Surgeons of England, Biochemical Society Transactions, pp. 871–873, Mar. 1990.

(List continued on next page.)

*Primary Examiner*—Leon B. Lankford, Jr.
(74) *Attorney, Agent, or Firm*—John W. Carpenter; Carpenter & Kulas, LLP (57) ABSTRACT

A dehydrated composition is provided that includes freeze-dried platelets. The platelets are loaded with trehalose which preserves biological properties during freeze-drying and rehydration. The trehalose loading is conducted at a temperature of from greater than about 25° C. to less than about 40° C., most preferably at 37° C., with the loading solution having trehalose in an amount from about 10 mM to about 50 mM. These freeze-dried platelets are substantially shelf-stable and are rehydratable so as to have a normal response to an agonist, for example, thrombin, with virtually all of the platelets participating in clot formation within about three minutes at 37° C.

45 Claims, 5 Drawing Sheets

OTHER PUBLICATIONS

A.A. Rayos et al., "Quick Freezing of Unfertilized Mouse Oocytes Using Ethylene Glycol with Sucros or Trehalose", Department of Theriogenology, Faculty of Veterinary Medicine, Hokkaido University, Japan, Journal of Reproduction and Fertility, pp. 123–129, Mar. 1993.

Ali, A.M. et al., "Platelet Concentrates Stored for 5 Days in a Reduced Volume of Plasma Maintain Hemostatic Function and Viability", The Canadian Red Cross Society and the Departments of Pathology, Medicine and Clinical Epidemiology and Biostatistics, McMaster University Faculty of Health Science, Hamilton, Ontario Canada, vol. 34, No. 1, 1994.

Allain, J.P. et al., "Platelets Fixed with Paraformaldehyde: A New Reagent for Assay of Von Willebrand Factor and Platelet Aggregating Factor", Department of Pathology, University of North Carolina, J. Lab. Clin. Med., vol. 85, No. 2, pp. 318–328, Feb. 1975.

Argall, Mary E. and Smith, Geoffrey D., "The Use of Trehalose–Stabilized Lyophilized Methanol Dehydrogenase from Hypomicrobium X for the Detection of Methanol", Division of Biochemistry and Molecular Biology, School of Life Sciences, Faculty of Science, The Australian National University, Canberra, Australia, vol. 30, No. 3, Jul. 1993.

Bando, Toru, et al., "Effects of Newly Developed Solutions Containing Trehalose on Twenty–hour Canine Lung Preservation", Department of Thoracic Surgery, Chest Disease Research Institute, Kyoto University, Kyoto, Japan, vol. 108, No. 1, pp. 92–98, Jul. 1994.

Bando, T. et al., "Twenty–Hour Canine Lung Preservation Using Newly Developed Solutions Containing Trehalose", Transplantation Proceedings, vol. 26, No. 2, pp. 871–872, Apr. 1994.

Blajchman, Morris A. et al., "The Contribution of the Haematocrit to Thrombocytopenic Bleeding in Experimental Animals", Departments of Pathology and Medicine, McMaster university and the Canadian Red Cross Society, Ontario, Canada, British Journal of Haematology 86, pp. 347–350, 1994.

Blakeley, Diane et al., "Dry Instant Blood Typing Plate for Bedside Use", The Lancet 336, pp. 854–855, 1990.

Bock, M. et al., "Cryopreservation of Human Platelets with Dimethyl Sulfoxide: Changes in Biochemistry and Cell Function", Department of Transfusion Medicine, University of Magdeburg, Magdeburg, Germany and the Transfusion Center, Klinikum Grosshadern, University of Munich, Transfusion 35, pp. 921–924, 1995.

Bode, Arthur P. et al., "Sustained Elevation of Intracellular Cyclic 3'–5' Adenosine Monophosphate is Necessary for Preservation of Platelet Integrity During Long–Term Storage at 22° C.", Departments of Pathology and Laboratory Medicine and Surgery, East Carolina University School of Medicine, vol. 83, No. 5, pp. 1235–1243, Mar. 1994.

Bode, Arthur P. and Miller, David T. "The Use of Thrombin Inhibitors and Aprotinin in the Preservation of Platelets Stored for Transfusion", Department of Clinical Pathology and Diagnostic Medicine, East Carolina University School of Medicine, pp. 753–758, Jun. 1989.

Colaco, Camilo et al., "Extraordinary Stability of Enzymes Dried in Trehalose: Simplified Molecular Biology", Quadrance Research Foundation, Biotechnology vol. 10, pp. 1007–1011, Sep. 1992.

Colaco, C. et al., "Trehalose Stabilisation of Biological Molecules", Quadrant Research Foundation, Biotechnology International pp. 345–350.

Carpenter, John F. et al., "Cryoprotection of Phosphofructokinase with Organic Solutes: Characterization of Enhanced Protection in the Presence of Divalent Cations", Department of Zoology, University of California, Davis, Archives of Biochemistry and Biophysics, vol. 250, No. 2, pp. 505–512, Nov. 1986.

Chao, F.C., et al., "Infusible Platelet Membrane Microvesicles: A Potential Transfusion Substitute for Platelets", Transfusion, vol. 36 No. 6, pp. 536–542, 1996.

Colvin, B.T., et al., "Effect of Dry Heating of Coagulation Factor Concentrates at 80° C. for 72 Hours on Transmission of Non–A, Non–B Hepatitis" The Lancet, pp. 814–816, Oct., 1988.

Crook, M. and Crawford, N., "Platelet Surface Charge Heterogeneity: Characterization of Human Platelet Subpopulations Separated by High Voltage Continuous Flow Electrophoresis", British Journal of Haematology 69, pp. 265–273, 1988.

Crowe, John H. et al., "Are Freezing and Dehydration Similar Stress Vectors? A Comparison of Modes of Interaction of Stabilizing Solutes with Biomolecules", Symposium on Cryosensitizing and Cryoprotective Agents at the $26^{th}$ Annual Meeting of the Society for Cryobiology, 27, pp. 219–231, 1990.

Crowe, John H. et al., Cryoprotection of Phosphofructokinase with Organic Solutes: Characterization of Enhanced Protection in the Presence of Divalent Cations:, Department of Zoology, University of California, Davis, Archives of Biochemistry and Biophysics, vol. 250, No. 2, pp. 505–512, Nov. 1986.

Crowe, John W. et al., "Is Vitrification Involed in Depression of the Phase Transition Temperature in Dry Phospholipids?", Biochimica et Biophysica Acta (BBA) 1280, pp. 187–196, 1996.

Crowe, John H. and Crowe, Lois M., "Preservation of Liposomes by Freeze–Drying" Liposome Technology, vol. 1, Chapter 14, pp. 229–252, 1993.

Crowe, John H. et al., "Preservation of Membranes in Anhydrobiotic Organisms: The Role of Trehalose", American Association for the Advancement of Science, vol. 223, pp. 701–703, Feb., 1984.

Crowe, John H. et al., "Preservation of Structural and Functional Activity in Lyophilized Sarcoplasmic Reticulum", Archives of Biochemistry and Biophysics, vol. 220, No. 2, pp. 477–484, Feb. 1983.

Crowe, Lois M. et al., "Effects of Carbohydrates on Membrane Stability at Low Water Activities"Department of Zoology, University of California, Davis, Biochemica et Biophysica Acta, 769, pp. 141–150, 1984.

Crowe, Lois M. et al., "Preservation of Freeze–Dried Liposomes by Trehalose", Department of Zoology, University of California, Davis, Archives of Biochemistry and Biophysics, vol. 242, No. 1, pp. 240–247, Oct., 1985.

Dale, George L. et al, "High–Efficiency Entrapment of Enzymes in Resealed Red Cell Ghosts by Dialysis", Academic Press, Inc., Methods in Enzymology, vol. 149, pp. 229–234, 1987.

Eleutherio, Elis C.A., "Role of the Trehalose Carrier in Dehydration Resistance of *Saccharomyces Cerevisiae*", Biochimica et Biophysica Acta, 1156, pp. 263–166, 1993.

Foote, R.H. et al., "Fertility of Bull Spermatozoa Frozen in Whole Milk Extender with Trehalose, Taurine, or Blood Serum", Department of Animal Science Cornell University and Eastern Artificial Insemination Cooperative, Inc., Ithaca, New York, Journal of Dairy Science, vol. 76, No. 7, 1993.

Gerencser, George A., "Cryoprotection of Aplysia Gut Basolateral Membranes by Trehalose", Department of Physiology, College of Medicine, University of Floride, Comp. Biochem. Physiol. Vol. 108A, No. I, pp. 53–57, 1994.

Goodrich, Raymond P. et al., "Preservation of Metabolic Activity in Lyophilized Human Erythrocytes", Proc. Natl. Acad. Sci. vol. 89, pp. 967–971, Feb., 1992.

Hirata, T. et al., "Effects of Trehalose in Canine Lung Preservation", Department of Thoracic Surgery, Chest Disease Research Institute, Kyoto University, Kyoto, Japan, vol. 115, No. 1, pp. 102–107, Jan. 1994.

Hirata, T. et al., "Effects of Trehalose in Preservation of Canine Lung for Transplants", Department of Thoracic Surgery, Chest Disease Research Institute, Kyoto University, Kyoto, Japan, Thorac. Cardiovasc. Surgeon 41, pp. 59–63, 1993.

Hirata, T. et al., "Successful 12–Hour–Lung Preservation with Trehalose", Transplantation Proceedings, vol. 25, No. 1, pp. 1597–1598, Feb. 1993.

Holme, S. et al., "Evaluation of Platelet Concentrates Stored for 5 days with Reduced Plasma Volume", American Red Cross, Mid–Atlantic Region and Eastern Virginia Medical School, Transfusion, vol. 34, No. 1, pp. 39–43, 1994.

Holme, S. et al., "Improved Maintenance of Platelet in vivo Viability During Storage When Using a Synthetic Medium with Inhibitors", American Red Cross, East Carolina University School of Medicine, vol. 119, No. 2, pp. 144–150, Feb. 1992.

Hottiger, Thomas et al., "The Role of Trehalose Synthesis for the Acquistion of Thermotolerance in Yeast II. Physiological Concentrations of Trehalose Increase the Thermal Stability of Protein In Vitro", Eur. J. Biochem. 219, pp. 187–193, 1994.

Hughes, K. and Crawford, N., "Reversible Electropermeabilisation of Human and Rat Blood Platelets: Evaluation of Morphological and Functional Integrity 'In Vitro' and 'In Vivo'", Department of Biochemistry and Cell Biology, Hunterian Institute, Royal College of Surgeon of England, Biochimica et Biophysica Acta, 981, pp. 277–287, 1989.

Ihler, Garret M. and Tsang, Hannah Chi–Wan, "Hypotonic Hemolysis Methods for Entrapment of Agents in Resealed Erythrocytes", Methods of Enzymology, vol. 149, pp. 221–229, 1987.

Jindal Rahul and Gray, Derek, "Preservation and Storage of Pancreatic Islets", Division of Transplantation, Mt. Sinai School of Medicine, New York and University of Oxford, United Kingdom, vol. 57, pp. 317–321, No. 3, Feb. 1994.

Leslie, Samuel B. et al., "Trehalose and Sucrose Protect Both Membranes and Proteins in Intact Bacteria during Drying", Section of Molecular and Cellular Biology, University of California, Davis, Applied and Environmental Microbiology, pp. 3592–3597, Oct., 1995.

Lionetti, F.J. et al., "Improve Method for the Cryopreservation of Human Red Cells in Liquid Nitrogen with Hydroxythyl Starch", Center for Blood Research and Tufts University School of Medicine, Boston, MA, Cryobiology 13, pp. 489–499, 1976.

Magnani, Mauro et al., "Targeting Antiretroviral Nucleoside Analogues in Phosphorylated Form to Macrophages: in Vitro and in Vivo Studies", Proc. Natl. Acad. Sci., vol. 89, pp. 6477–6481, Jul. 1992.

Moroff, G. et al., "Effect on Platelet Properties of Exposure to Temperatures Below 20° C. for Short Periods During Storage at 20 to 24° C.", American Red Cross, Jerome H. Holland Laboratory for the Biomedical Sciences, and Red Cross Blood Services, Transfusion, vol. 34, No. 4, pp. 317–321, 1994.

Okada, Craig Y. and Rechsteiner, Martin, "Introduction of Macromolecules into Cultured Mammalian Cells by Osmotic Lysis of Pinocytic Vesicles", Department of Biology, University of Utah, vol. 29, pp. 33–41, May 1982.

Puisieux, Francis et al., "Liposomes, New Systems and New Trends in their Applications", Published in France by Editions de Sante, Chapter 8, pp. 239–272, 1995.

Read, Marjorie S. et al., "Preservation of Hemostatic and Structural Properties of Rehydrated Lyophilized Platelets: Potential for Long–Term Storage of Dried Platelets for Transfusion", Proc. Natl. Acad. Sci, vol. 92, pp. 397–401, Jan. 1995.

Rechsteiner, Martin, "Osmotic Lysis of Pinosomes", Methods in Enzymology, vol. 149, pp. 42–48, 1987.

Roser, Bruce and Colaco, Camilo, "A Sweeter Way to Fresher Food", New Scientist, May 1993.

Roser, Bruce, "Trehalose, a New Approach to Premium Dried Foods", Trends in Food Science & Technology Jul. 1991.

Rudolph, Alan S. and Crowe, John H., "A Calorimetric and Infrared Spectroscopic Study of the Stabilizing Solute Proline", Biophysical Society, vol. 50, pp. 423–430, Sep. 1986.

Shier, W. Thomas, "Studies on the Mechanisms of Mammalian Cell Killing by a Freeze–Thaw Cycle: Conditions that Prevent Cell Killing Using Nucleated Freezing", Department of Medicinal Chemistry and Pharmacognosy, College of Pharmacy, University of Minnesota, Cryobiology 25, pp. 110–120 (1988).

Tablin, Fern et al., "Membrane Phase of Intact Human Platelets: Correlation with Cold–Induced Activation", Departments of Anatomy, Physiology, and Cell Biology and Molecular and Cellular Biology, University of California, Davis, Journal of Cellular Physiology 168, pp. 305–313, 1996.

Terasaki, Mark et al., "Localization of Endoplasmic Reticulum in Living and Glutaraldehyde–Fixed Cells with Fluroescent Dyes", Dana–Farber Cancer Institute and Department of Pathology Harvard Medical School, Cell, vol. 38, pp. 101–108, Aug. 1984.

Yokomise, H. et al., "Reliable Cryopreservation of Trachea for One Month in a New Trehalose Solution", Division of Thoracic Surgery, Chest Disease Research Institute, Kyoto University, Kyoto, Japan, vol. 110, No. 2, pp. 382–385, 1995.

Verma, et al., "Gene therapy—promises, problems and prospects," Nature, vol. 389, pp. 239–242, Sep. 18, 1997.

Eck, et al., "Gene–Based Therapy," Goodman & Gilman's The Pharmacological Basis of Therapeutics, $9^{th}$ Edition, McGraw–Hill, pp. 77–101, (1996).

Andrews et al., "Molecular Mechanism of Platelet Adhesion and Activation," *Int. J. Biochem, Cell. Biol.,* 29 (1), pp. 91–105 (1997).

Beattie et al., "Trehalose: A Cryoprotectant that Enhances Recovery and Preserves Function of Human Pancreatic Islets after Long–Term Storage," *Diabetes, 46,* pp. 519–523 (1997).

Böck et al., "Cryopreservation of Human Platelets with Dimethyl Sulfoxide: Changes in Biochemistry and Cell Function," *Transfusion, 35* pp. 921–924 (1995).

Crowe, et al., "Anhydrobiosis," *Annu. Rev. Physiol., 54,* pp. 579–599 (1992).

Leslie et al., "Trehalose Lowers Membrane Phase Transitions in Dry Yeast Cells," *Biochimica et Biophysica Acta, 1192,* pp. 7–13 (1994).

Owners, et al., "The Role of Platelet Microparticles in Hemostasis," *Transfusion Medicine Reviews, 8* (1), pp. 37–44 (1994).

Read et al., "Preservation of Hemostatic and Structural Properties of Rehydrated Lyophilized Platelets: Potential for Long–term Storage of Dried Platelets for Transfusion," *Proc. Natl. Acad. Sci. USA,* 92, pp. 397–401 (1995).

Tablin et al., "Membrane Phase Transition of Intact Human Platelets: Correlation with Cold–Induced Activation," *J. Cellular Physicol,* 168, pp. 305–313 (1996).

Valeri et al., "A Simple Method of Freezing Human Platelets Using 6% Dimehtylsulfoxide and Storage at –80° C.," *Blood, 43* (1), pp. 131–136 (1974).

THERAPEUTIC PLATELETS AND METHODS

This is a continuation patent application of copending patent application Ser. No. 09/501,773, filed Feb. 10, 2000.

STATEMENT REGARDING FEDERAL SPONSORED RESEARCH AND DEVELOPMENT

This invention was made with Government support under Grant Nos. HL57810-03 and HL61204-02, awarded by the National Institutes of Health. The Government has certain rights in this invention.

FIELD OF THE INVENTION

The present invention generally relates to the therapeutic uses of blood platelets, and more particularly to manipulations or modifications of platelets, such as in preparing freeze-dried compositions that can be rehydrated at the time of application and which when rehydrated have a normal response to thrombin and other agonists with respect to that of fresh platelets. The inventive compositions are useful in applications such as transfusion therapy, as hemostasis aids and for drug delivery.

BACKGROUND OF THE INVENTION

Blood transfusion centers are under considerable pressure to produce platelet concentrates for transfusion. The enormous quest for platelets necessitates storage of this blood component, since platelets are important contributors to hemostasis. Platelets are generally oval to spherical in shape and have a diameter of 2–4 μm. Today platelet rich plasma concentrates are stored in bloodbags at 22° C.; however, the shelf life under these conditions is limited to five days. The rapid loss of platelet function during storage and risk of bacterial contamination complicates distribution and availability of platelet concentrates. Platelets tend to become activated at low temperatures. When activated they are substantially useless for an application such as transfusion therapy. Therefore the development of preservation methods that will increase platelet lifespan is desirable.

Several techniques for preservation of platelets have been developed over the past few decades. Cryopreservation of platelets using various agents, such as glycerol (Valeri et al., *Blood,* 43, 131–136, 1974) or dimethyl sulfoxide, "DMSO" (Bock et al., *Transfusion,* 35, 921–924, 1995), as the cryoprotectant have been done with some success. The best results have been obtained with DMSO. However, a considerable fraction of these cells are partly lysed after thawing and have the shape of a balloon. These balloon cells are not responsive to various agonists, so that overall responsiveness of frozen thawed platelets to various agonists is reduced to less than 35% compared with fresh platelets. The shelf life of cryopreserved DMSO platelets at −80° C. is reported to be one year, but requires extensive washing and processing to remove cryoprotective agents, and even then the final product has a severe reduction in ability to form a clot.

Attempts to dry platelets by lyophilization have been described with paraformaldehyde fixed platelets (Read et al., *Proc. Natl. Acad. Sci. USA,* 92, 397–401, 1995). U.S. Pat. No. 5,902,608, issued May 11, 1999, inventors Read et al. describe and claim a surgical aid comprising a substrate on which fixed, dried blood platelets are carried. These dried blood platelets are fixed by contacting the platelets to a fixative such as formaldehyde, paraformaldehyde, gutaraldehyde, or permanganate. Proper functioning of lyophilized platelets that have been fixed by such fixative agents in hemostasis is questionable.

Spargo et al., U.S. Pat. No. 5,736,313, issued Apr. 7, 1998, have described a method in which platelets are loaded overnight with an agent, preferably glucose, and subsequently lyophilized. The platelets are preincubated in a preincubation buffer and then are loaded with carbohydrate, preferably glucose, having a concentration in the range of about 100 mM to about 1.5 M. The incubation is taught to be conducted at about 10° C. to about 37° C., most preferably about 25° C.

U.S. Pat. No. 5,827,741, Beattie et al., issued Oct. 27, 1998, discloses cryoprotectants for human platelets, such as dimethylsulfoxide and trehalose. The platelets may be suspended, for example, in a solution containing a cryoprotectant at a temperature of about 22° C. and then cooled to below 15° C. This incorporates some cryoprotectant into the cells.

Trehalose is a disaccharide found at high concentrations in a wide variety of organisms that are capable of surviving almost complete dehydration (Crowe et al., *Anhydrobiosis. Annu. Rev. Physiol.,* 54, 579–599, 1992). Trehalose has been shown to stabilize certain cells during freezing and drying (Leslie et al., *Biochim. Biophys. Acta,* 1192, 7–13, 1994; Beattie et al., *Diabetes,* 46, 519–523, 1997).

Other workers have sought to load platelets with trehalose through use of electroporation before drying under vacuum. However, electroporation is very damaging to the cell membranes and is believed to activate the platelets. Activated platelets have dubious clinical value.

Platelets have also been suggested for drug delivery applications in the treatment of various diseases, as is discussed by U.S. Pat. No. 5,759,542, issued Jun. 2, 1998, inventor Gurewich. This patent discloses the preparation of a complex formed from a fusion drug including an A-chain of a urokinase-type plasminogen activator that is bound to an outer membrane of a platelet.

Accordingly, a need exists for the effective and efficient preservation of platelets such that they maintain, or preserve, their biological properties, particularly their response to platelet agonists such as thrombin, and which can be practiced on a large, commercially feasible scale. Further, it would also be useful to expand the types of present vehicles that are useful for encapsulating drugs and used for drug delivery to targeted sites.

SUMMARY OF THE INVENTION

In one aspect of the present invention, a dehydrated composition is provided comprising freeze-dried platelets that are effectively loaded with trehalose to preserve biological properties during freeze-drying and rehydration. These platelets are rehydratable so as to have a normal response to at least one agonist, such as thrombin. For example, substantially all freeze-dried platelets of the invention when rehydrated and mixed with thrombin (1 U/ml) form a clot within three minutes at 37° C. The dehydrated composition can include one or more other agents, such as antibiotics, antifungals, growth factors, or the like, depending upon the desired therapeutic application.

Embodiments of the present invention provide a process for preparing a dehydrated composition comprising disposing platelets in an oligosaccharide solution for loading an oligosaccharide from the oligosaccharide solution into the platelets, preventing a decrease in a loading efficiency gradient in the loading of the oligosaccharide into the platelets, and lyophilizing the platelets. The preventing a decrease in a loading efficiency gradient in the loading of the oligosaccharide into the platelets may comprise maintaining a concentration of the oligosaccharide in the oligosaccharide solution below about 50 mM. The preventing a decrease in a loading efficiency gradient in the loading of the oligosaccharide into the platelets may also comprise maintaining a positive gradient of loading efficiency (%) to concentration (mM) of the oligosaccharide in the oligosaccharide solution.

Embodiments of the present invention also provide a process for preparing a dehydrated composition comprising disposing platelets in an oligosaccharide solution for loading an oligosaccharide from the oligosaccharide solution into the platelets, preventing a decrease in a loading gradient in the loading of the oligosaccharide into the platelets, and lyophilizing the platelets. The preventing a decrease in a loading gradient in the loading of the oligosaccharide into the platelets may comprise maintaining a concentration of the oligosaccharide in the oligosaccharide solution below about 50 mM. The preventing a decrease in a loading gradient in the loading of the oligosaccharide into the platelets may also comprise maintaining a positive gradient of concentration of oligosaccharide loaded into the platelets to concentration of the oligosaccharide in the oligosaccharide solution.

In another aspect of the invention, a hemostasis aid is provided where the above-described freeze-dried platelets are carried on or by a biocompatible surface. A further component of the hemostasis aid may be a therapeutic agent, such as an antibiotic, an antifungal, or a growth factor. The biocompatible surface may be a bandage or a thrombic surface, such as freeze-dried collagen. Such a hemostasis aid can be rehydrated just before the time of application, such as by hydrating the surface on or by which the platelets are carried, or, in case of an emergency, the dry hemostasis treatment aid could be applied directly to the wound or burn and hydrated in situ.

Methods of making and using inventive embodiments are also described. One such method is a process of preparing a dehydrated composition comprising providing a source of platelets, effectively loading the platelets with trehalose to preserve biological properties, cooling the trehalose loaded platelets to below their freezing point, and lyophilizing the cooled platelets. The trehalose loading includes incubating the platelets at a temperature from greater than about 25° C. to less than about 40° C. with a trehalose solution having up to about 50 mM trehalose therein. The process of using such a dehydrated composition further may comprise rehydrating the platelets. The rehydration preferably includes a prehydration step wherein the freeze-dried platelets are exposed to warm, moisture saturated air for a time sufficient to bring the water content of the freeze-dried platelets to between about 35 weight percent to about 50 weight percent.

In yet another aspect of the invention, a drug delivery composition is provided comprising platelets having a homogeneously distributed concentration of a therapeutic agent therein. The drug delivery composition is particularly useful for targeting the encapsulated drug to platelet-mediated sites.

Practice of the invention permits the manipulation or modification of platelets while maintaining, or preserving, biological properties, such as a response to thrombin. Further, use of the method to preserve platelets can be practiced on a large, commercially feasible scale, and avoids platelet activation. The inventive freeze-dried platelets, and hemostasis aids including the freeze-dried platelets, are substantially shelf stable at ambient temperatures when packaged in moisture barrier materials.

DETAILED DESCRIPTION OF THE PREFERRED EMBODIMENTS

Compositions and embodiments of the invention include platelets that have been manipulated (e.g. by freeze-drying) or modified (e.g. loaded with drugs), and that are useful for therapeutic applications, particularly for platelet transfusion therapy, as surgical or hemostasis aids, such as wound dressings, bandages, and as sutures, and as drug-delivery vehicles. As has been known, human platelets have a phase transition between 12° C. and 20° C. We have found that platelets have a second phase transition between 30° C. and 37° C. Our discovery of this second phase transition temperature range suggests the possible use of platelets as vehicles for drug delivery because we can load platelets with various useful therapeutic agents without causing abnormalities that interfere with normal platelet responses due to changes, such as in the platelet outer membranes.

For example, platelets may be loaded with anti-thrombic drugs, such as tissue plasminogen activator (TPA) so that the platelets will collect at the site of a thrombus, as in an heart attack, and release the "clot busting" drug or drugs that are encapsulated and have been targeted by the platelets. Antibiotics can also be encapsulated by the platelets, since lipopolysaccharides produced by bacteria attract platelets.

Antibiotic loaded platelets will bring the selected antibiotics to the site of inflammation. Other drugs that can be loaded include anti-mitotic agents and antiangiogenic agents. Since platelets circulate in newly formed vessels associated with tumors, they could deliver anti-mitotic drugs in a localized fashion, and likely platelets circulating in the neovasculature of tumors can deposit anti-angiogenic drugs so as to block the blood supply to tumors. Thus, platelets loaded with a selected drug in accordance with this invention can be prepared and used for therapeutic applications. The drug-loaded platelets are particularly contemplated for blood-borne drug delivery, such as where the selected drug is targeted to a site of platelet-mediated forming thrombi or vascular injury. The so-loaded platelets have a normal response to at least one agonist, particularly to thrombin. Such platelets can be loaded additionally with trehalose, if preservation by freeze-drying is intended.

The key component for compositions and apparatus of the invention, when preservation will be by freeze-drying, is an oligosaccharide, preferably trehalose, because we have found that platelets which are effectively loaded with trehalose preserve biological properties during freeze-drying (and rehydration). This preservation of biological properties, such as the normal clotting response in combination with thrombin, is necessary so that the platelets following preservation can be successfully used in a variety of therapeutic applications.

Normal hemostasis is a sequence of interactions in which blood platelets contribute, beginning with adhesion of platelets to an injured vessel wall. The platelets form an aggregate that accelerates coagulation. A complex, termed the glycoprotein (GP) 1b-IX-V complex, is involved in platelet activation by providing a binding site on the platelet surface for the potent agonist, α-thrombin. α-thrombin is a serine protease that is released from damaged tissue. Thus, it is important that the manipulations and modifications in accordance with this invention do not activate the platelets. Further, it is normally preferred that the platelets be in a resting state. Otherwise, the platelets will activate.

Although for most contemplated therapeutic applications the clotting response to thrombin is key, the inventive freeze-dried platelets after rehydration will also respond to other agonists besides thrombin. These include collagen, ristocetin, and ADP (adenosine diphosphate), all of which are normal platelet agonists. These other agonists typically pertain to specific receptors on the platelet's surface.

Broadly, the preparation of preserved platelets in accordance with the invention comprises the steps of providing a source of platelets, loading the platelets with a protective oligosaccharide at a temperature above about 25° C. and less than about 40° C., cooling the loaded platelets to below −32° C., and lyophilizing the platelets.

In order to provide a source of platelets suitable for the inventive preservation process, the platelets are preferably isolated from whole blood. Thus, platelets used in this invention preferably have had other blood components (erythrocytes and leukocytes) removed prior to freeze-drying. The removal of other blood components may be by procedures well known to the art, which typically involve a centrifuge step.

Figure 1:
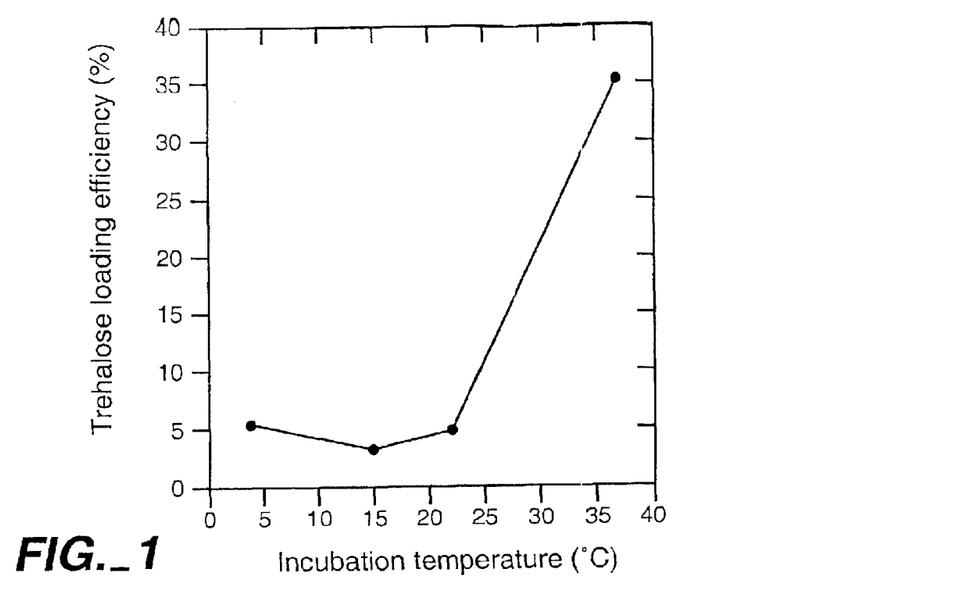
FIG. 1 graphically illustrates the loading efficiency of trehalose plotted versus incubation temperature of human platelets.
Figure 2:
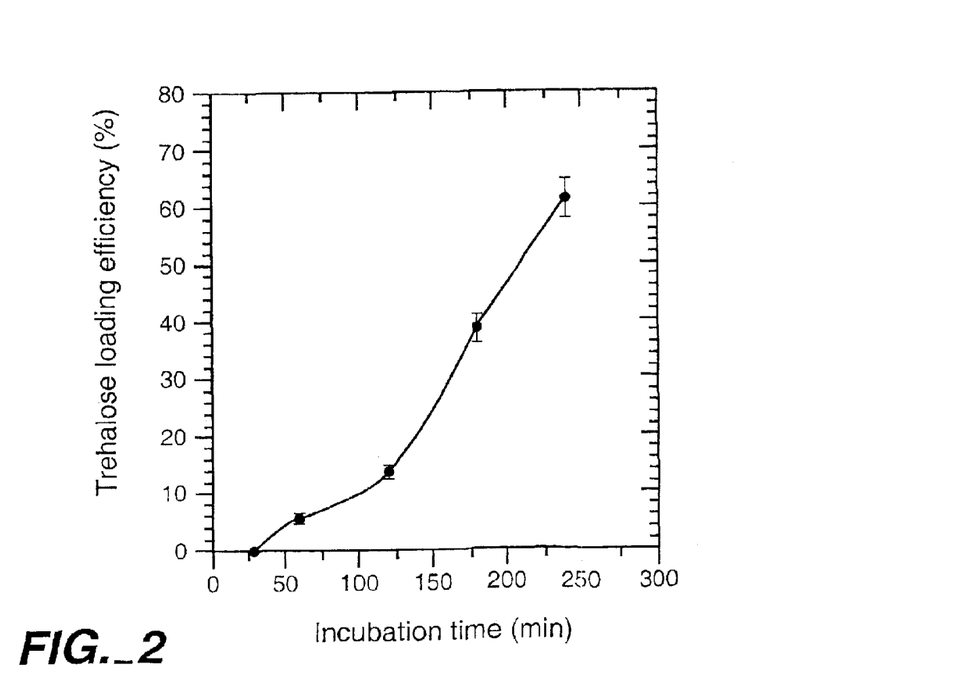
FIG. 2 graphically illustrates the percentage of trehalose-loaded human platelets following incubation as a function of incubation time.

The amount of the preferred trehalose loaded inside the inventive platelets is from about 10 mM to about 50 mM, and is achieved by incubating the platelets to preserve biological properties during freeze-drying with a trehalose solution that has up to about 50 mM trehalose therein. Higher concentrations of trehalose during incubation are not preferred, as will be more fully explained later. The effective loading of trehalose is also accomplished by means of using an elevated temperature of from greater than about 25° C. to less than about 40° C., more preferably from about 30° C. to less than about 40° C., most preferably about 37° C. This is due to the discovery of the second phase transition for platelets. As can be seen by FIG. 1, the trehalose loading efficiency begins a steep slope increase at incubation temperatures above about 25° C. up to about 40° C. The trehalose concentration in the exterior solution (that is, the loading buffer) and the temperature during incubation together lead to a trehalose uptake that seems to occur primarily through fluid phase endocytosis (that is, pinocytosis). Pinocytosed vesicles lyse over time, which results in a homogeneous distribution of trehalose in the platelets, does not activate the platelets, and can be applied for large scale production. FIG. 2 illustrates the trehalose loading efficiency as a function of incubation time.

As may be gathered from various of the figures, in preparing particularly preferred embodiments, platelets may be loaded with trehalose by incubation at 37° C. for about four hours. The trehalose concentration in the loading buffer is preferably 35 mM, which results in an intracellular trehalose concentration of around 20 mM, but in any event is most preferably not greater than about 50 mM trehalose. At trehalose concentrations below about 50 mM, platelets have a normal morphological appearance.

Human platelets have a phase transition between 12° C. and 20° C. We found relatively poor loading when the platelets were chilled through the phase transition. Thus, in practicing the method described by U.S. Pat. No. 5,827,741, of which some of us are coinventors, only a relatively modest amount of trehalose may be loaded into platelets.

In this application, we have further investigated the phase transition in platelets and have found a second phase transition between 30° C. and 37° C. We believe that the excellent loading we obtain at about 37° C. is in some way related to this second phase transition. Without being limited by theory, we also believe that pinocytosis is involved, but it may be that the second phase transition itself stimulates the pinocytosis at high temperatures. It may be that other oligosaccharides when loaded in this second phase transition in amounts analogous to trehalose could have similar effects.

In any case, it is fortuitous that the loading can be done at elevated temperatures in view of the fact that chilling platelets slowly—a requirement for using the first, or lower, phase transition between 20° C. and 12° C. to introduce trehalose—is well known to activate them (Tablin et al., *J. Cell. Physiol.*, 168, 305–313, 1996). Our relatively high temperature loading, regardless of the mechanism, is thus unexpectedly advantageous both by providing increased loading as well as surprisingly, obviating the activation problem.

Figure 6:
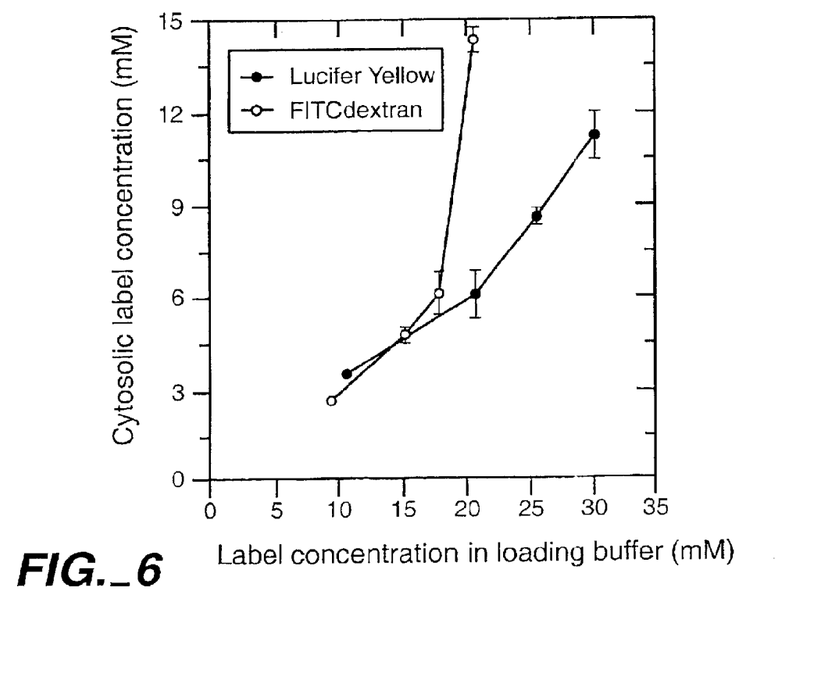
FIG. 6 graphically illustrates the uptake of FITC dextran versus the external concentration compared with that of the marker, LYCH (with an incubation time of four hours)

Turning to FIG. 6, one sees that we have loaded other, larger molecules into the platelets. In FIG. 6 an illustrative large molecule (FITC dextran) was loaded into the platelets. This illustrates that a wide variety of water-soluble, therapeutic agents can be loaded into the platelets by utilizing the second phase transition, as we have shown may be done with trehalose and with FITC dextran, while still maintaining characteristic platelet surface receptors and avoiding platelet activation.

We have achieved loading efficiencies by practicing the invention with values as high as 61% after four hours incubation. The plateau is not yet reached after four hours. The high loading efficiency of trehalose is a strong indication that the trehalose is homogeneously distributed rather than located in pinocytosed vesicles, and we expect similar results for loading other therapeutic agents. A loading efficiency of 61% in an external concentration of 25 mM corresponds to a cytosolic concentration of 15 mM. If trehalose was only located in endosomes of 0.1 micrometer, the vesiculation number would be more than 1000. It is unlikely that such a high number of vesicles would be present in platelets next to the other platelet organelles. We therefore believe that the pinocytosed vesicles lyse in the cytoplasm. This results in a homogeneous distribution of trehalose rather than punctuated loading in small vesicles. It is also possible that the trehalose is crossing the membrane due to the phase transition between 30° C. and 37° C.

We have found that the endocytotic uptake route is blocked at sugar concentrations above 0.1 M. Consequently, we prefer not to use sugar concentrations higher than about 50 mM in the loading buffer, because at some point above this value we have found swelling and morphological changes of the platelets. Thus, we have found that platelets become swollen after four hours incubation at 37° C. in 75 mM trehalose. Further, at concentrations higher than 50 mM the internal trehalose concentration begins to decrease. By contrast to the present invention, the platelet method taught by Spargo et al., U.S. Pat. No. 5,736,313, loads with carbohydrate in the range beginning at about 100 mM and going up to 1.5 M. As noted, we find a high concentration of loading buffer, at least with trehalose, to lead to swelling and morphological changes.

The effective loading of platelets with trehalose is preferably conducted by incubating for at least about two hours, preferably for at least about four hours. After this loading, then the platelets are cooled to below their freezing point and lyophilized.

Before freezing, the platelets should be placed into a resting state. If not in the resting state, platelets would likely activate. In order to place the platelets in a resting state, a variety of suitable agents, such as calcium channel blockers, may be used. For example, solutions of adenine, adenosine or iloprost are suitable for this purpose. Another suitable agent is PGE1. It is important that the platelets are not swollen and are completely in the resting state prior to drying. The more they are activated, the more they will be damaged during freeze-drying.

After the platelets have been effectively loaded with trehalose and are in a resting state, then the loading buffer is removed and the platelets are contacted with a drying buffer. Drying of platelets after trehalose loading may be carried out by suspending the platelets in a solution containing a suitable water replacing molecule (or drying buffer), such as albumin. If albumin is used, it should be from the same species as the platelets. The drying buffer should also include trehalose, preferably in amounts up to about 100 mM. The trehalose in the drying buffer assists in spatially separating the platelet as well as stabilizing the platelet membranes on the exterior. The drying buffer preferably also includes a bulking agent (to further separate the platelets). As already mentioned, albumin may serve as a bulking agent, but other polymers may be used with the same effect. Suitable other polymers, for example, are water-soluble polymers such as HES and dextran.

The trehalose loaded platelets in drying buffer are then cooled to a temperature below about −32° C. A cooling, that is, freezing, rate is preferably between −30° C. and −1° C./min. and more preferably between about −2° C./min to −5° C./min.

The lyophilization step is preferably conducted at a temperature below about −32° C., for example conducted at about −40° C., and drying may be continued until about 95 weight percent of water has been removed from the platelets. During the initial stages of lyophilization, the pressure is preferably at about $1 \times 10^{-6}$ torr. As the samples dry, the temperature can be raised to be warmer than −32° C. Based upon the bulk of the sample, the temperature and the pressure it can be emperically determined what the most efficient temperature values should be in order to maximize the evaporative water loss. Freeze-dried compositions of the invention preferably have less than about 5 weight percent water.

The freeze-dried platelets may be used by themselves, dissolved in a physiologically acceptable solution, or may be a component of a biologically compatible (biocompatible) structure or matrix, which provides a surface on or by which the freeze-dried platelets are carried. The freeze-dried platelets can be, for example, applied as a coating to or impregnated in a wide variety of known and useful materials suitable as biocompatible structures for therapeutic applications. The earlier mentioned U.S. Pat. No. 5,902,608, for example, discusses a number of materials useful for surgical aid, wound dressings, bandages, sutures, prosthetic devices, and the like. Sutures, for example, can be monofilament or braided, can be biodegradable or nonbiodegradable, and can be made of materials such as nylon, silk, polyester, cotton, catgut, homopolymers, and copolymers of glycolide and lactide, etc. Polymeric materials can also be cast as a thin film, sterilized, and packaged for use as a wound dressing. Bandages may be made of any suitable substrate material, such as woven or nonwoven cotton or other fabric suitable for application to or over a wound, may optionally include a backing material, and may optionally include one or more adhesive regions on the face surface thereof for securing the bandage over the wound.

The freeze-dried platelets, whether by themselves, as a component of a vial-compatible structure or matrix, and optionally including other dry or freeze-dried components, may be packaged so as to prevent rehydration until desired. The packaging may be any of the various suitable packagings for therapeutic purposes, such as made from foil, metallized plastic materials, and moisture barrier plastics (e.g. high-density polyethylene or plastic films that have been created with materials such as SiOx), cooling the trehalose loaded platelets to below their freezing point, and lyophilizing the cooled platelets. The trehalose loading includes incubating the platelets at a temperature from greater than about 25° C. to less than about 40° C. with a trehalose solution having up to about 50 mM trehalose therein. The process of using such a dehydrated composition comprises rehydrating the platelets. The rehydration preferably includes a prehydration step sufficient to bring the water content of the freeze-dried platelets to between 35 weight percent to about 50 weight percent.

Figure 7:
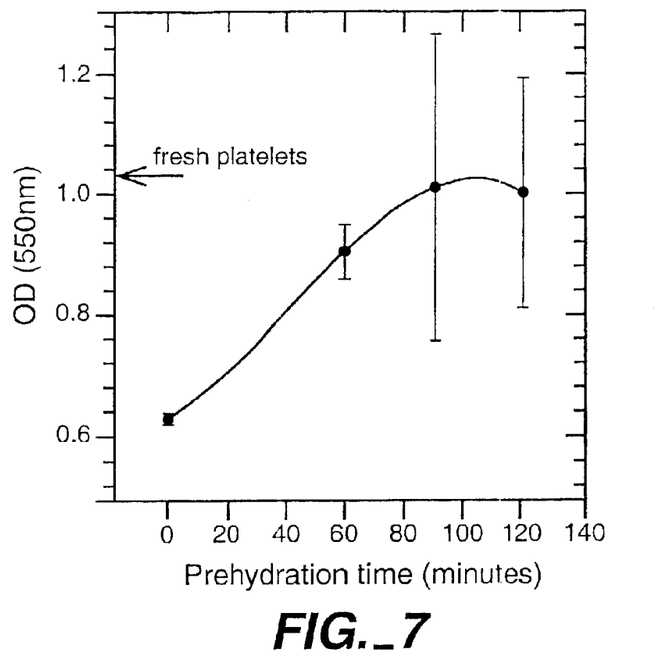
FIG. 7 graphically illustrates the effect of prehydration on optical density of platelets.

When reconstitution is desired, prehydration of the freeze-dried platelets in moisture saturated air followed by rehydration is preferred. Use of prehydration yields cells with a much more dense appearance and with no balloon cells being present. Prehydrated, previously lyophilized platelets of the invention resemble fresh platelets. This is illustrated, for example, by FIG. 7. As can be seen, the previously freeze-dried platelets can be restored to a condition that looks like fresh platelets.

Before the prehydration step, it is desirable to have diluted the platelets in the drying buffer to prevent aggregation during the prehydration and rehydration. At concentrations below about 3×10⁸ cells/ml, the ultimate recovery is about 70% with no visible aggregates. Prehydration is preferably conducted in moisture saturated air, most preferably is conducted at about 37° C. for about one hour to about three hours. The preferred prehydration step brings the water content of the freeze-dried platelets to between about 35 weight percent to about 50 weight percent.

The prehydrated platelets may then be fully rehydrated. Rehydration may be with any aqueous based solutions, depending upon the intended application. In one preferred rehydration, we have used plasma, which has resulted in about 90% recovery.

Since it is frequently desirable to dilute the platelets to prevent aggregation when the freeze-dried platelets are once again hydrated, it may then be desired or necessary for particular clinical applications to concentrate the platelets. Concentration can be by any conventional means, such as by centrifugation. In general, a rehydrated platelet composition will preferably have $10^6$ to $10^{11}$ platelets per ml, more preferably $10^8$ to $10^{10}$ platelets per ml.

By contrast with the previous attempts at freeze drying platelets, we show here that with a very simple loading, freeze-drying and rehydration protocol one obtains platelets that are morphologically intact after rehydration, and have an identical response to thrombin as do fresh platelets. Moreover, the concentration of thrombin to give this response is a physiological concentration—1 U/ml.

Figure 8A:
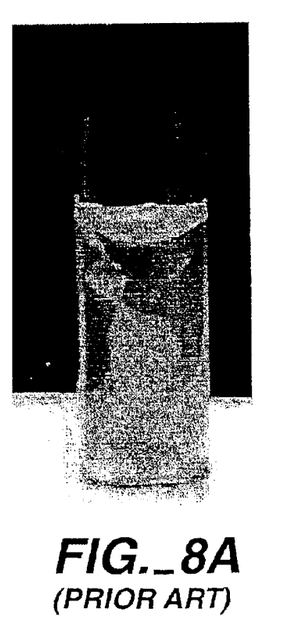
FIG. 8 illustrates the response of 500 $\mu$l platelets solution (with a platelet concentration of $0.5 \times 10^8$ cells/ml) that was transferred to aggregation vials, thrombin added (1 U/ml) to each sample, and the samples stirred for three minutes at 37° C., where panel (A) are the prior art platelets and panel (B) are the inventive platelets; and, FIG. 9 graphically illustrates clot formation where the absorbance falls sharply upon addition of thrombin (1 U/ml) and the platelet concentration drops from $250 \times 10^6$ platelets/ml to below $2 \times 10^6$ platelets/ml after three minutes for the inventive platelets.
Figure 8B:
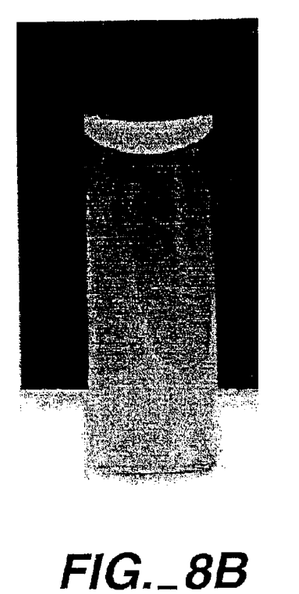

For example, FIG. 8, panel (A), illustrates the clot formation for fresh platelets and in panel (B) for platelets that have been preserved and then rehydrated in accordance with this invention. The cell counts that were determined after three minutes exposure to thrombin were zero for both the fresh platelets and the previously freeze-dried platelets of the invention.

Figure 9:
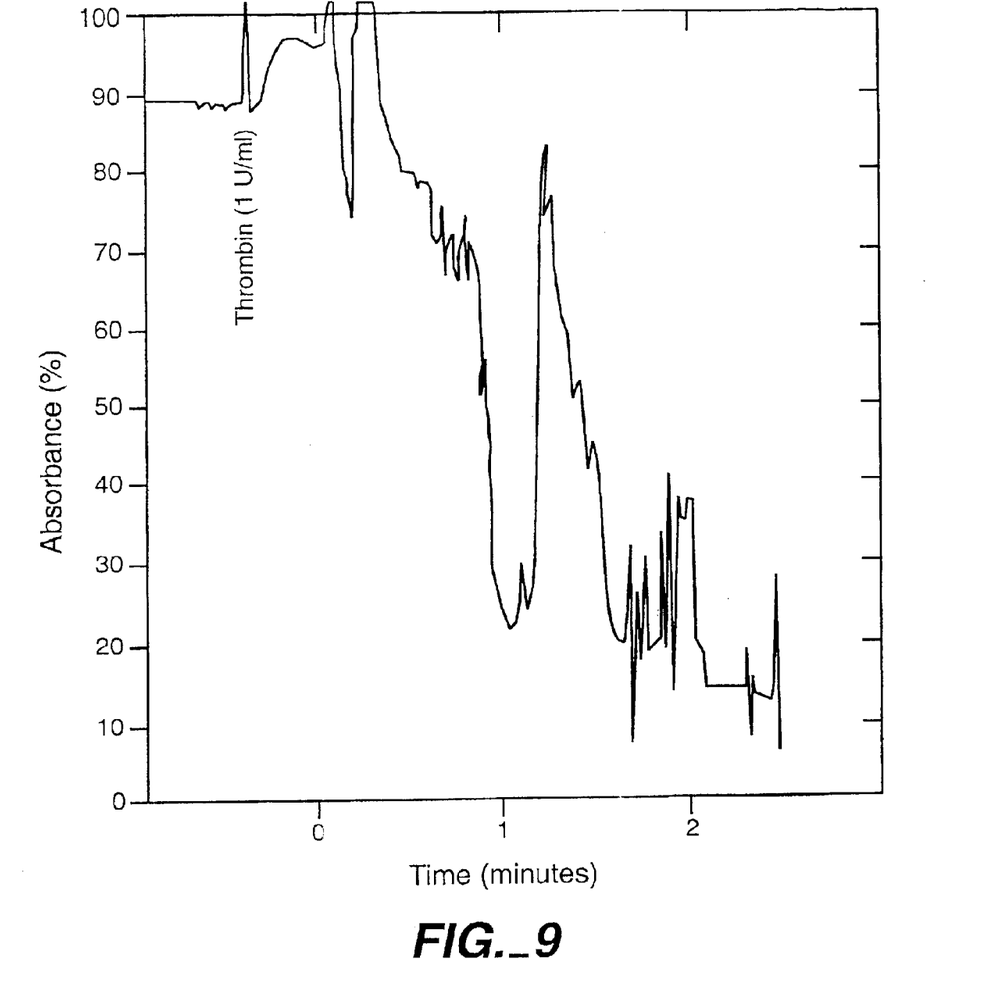

FIG. 9 graphically illustrates clotting as measured with an aggregometer. With this instrument one can measure the change in transmittance when a clot is formed. The initial platelet concentration was 250×10⁶ platelets/ml, and then thrombin (1 U/ml) was added and the clot formation was monitored with the aggregometer. The absorbance fell sharply and the cell count dropped to below 2×10⁶ platelets/ml after three minutes, which was comparable to the results when the test was run with fresh platelets as a control.

Although platelets for use in this invention preferably have had other blood components removed before freeze-drying, compositions and apparatuses of the invention may also include a variety of additional therapeutic agents. For example, particularly for embodiments contemplated in hemostasis applications, antifungal and antibacterial agents are usefully included with the platelets, such as being admixed with the platelets. Embodiments can also include admixtures or compositions including freeze-dried collagen, which provides a thrombogenic surface for the platelets. Other components that can provide a freeze-dried extracellular matrix can be used, for example, components composed of proteoglycan. Yet other therapeutic agents that may be included in inventive embodiments are growth factors. When the embodiments include such other components, or admixtures, they are preferably in dry form, and most preferably are also freeze-dried. We also contemplate therapeutic uses of the composition where additional therapeutic agents may be incorporated into or admixed with the platelets in hydrated form. The platelets, as earlier mentioned, can also be prepared as to encapsulate drugs in drug delivery applications. If trehalose is also loaded into the platelet interiors, then such drug-encapsulated platelets may be freeze-dried as has been earlier described.

The platelets should be selected of the mammalian species for which treatment is intended (e.g. human, equine, canine, feline, or endangered species), most preferably human.

The injuries to be treated by applying hemostasis aids with the platelets include abrasions, incisions, burns, and may be wounds occurring during surgery of organs or of skin tissue. The platelets of the invention may be applied or delivered to the location of such injury or wound by any suitable means. For example, application of inventive embodiments to burns can encourage the development of scabs, the formation of chemotactic gradients, of matrices for inducing blood vessel growth, and eventually for skin cells to move across and fill in the burn.

For transfusion therapy, inventive compositions may be reconstituted (rehydrated) as pharmaceutical formulations and administered to human patients by intravenous injection. Such pharmaceutical formulations may include any aqueous carrier suitable for rehydrating the platelets (e.g., sterile, physiological saline solution, including buffers and other therapeutically active agents that may be included in the reconstituted formulation). For drug delivery, the inventive compositions will typically be administered into the blood stream, such as by i.v.

Aspects of the invention will now be illustrated by the following examples, which are not intended to limit the invention. Abbreviations used in the examples, and elsewhere, are as follows.

DMSO=dimethylsulfoxide
ADP=adenosine diphosphate
PGE1=prostaglandin El
HES=hydroxy ethyl starch
EGTA=ethylene glycol-bis(2-aminoethyl ether) N,N,N',N',tetra-acetic acid
TES=N-tris (hydroxymethyl) methyl-2-aminoethane-sulfonic acid
HEPES=N-(2-hydroxyl ethyl) piperarine-N'-(2-ethanesulfonic acid)
PBS=phosphate buffered saline
HSA=human serum albumin

EXPERIMENTAL

EXAMPLE 1

Washing of Platelets.

Platelet concentrations were obtained from the Sacramento blood center or from volunteers in our laboratory. Platelet rich plasma was centrifuged for 8 minutes at 320×g to remove erythrocytes and leukocytes. The supernatant was pelleted and washed two times (480×g for 22 minutes, 480×g for 15 minutes) in buffer A (100 mM NaCl, 10 mM KCl, 10 mM EGTA, 10 mM imidazole, pH 6.8). Platelet counts were obtained on a Coulter counter T890 (Coulter, Inc., Miami, Fla.).

Loading of Lucifer Yellow CH into Platelets.

A fluorescent dye, lucifer yellow CH (LYCH), was used as a marker for penetration of the membrane by a solute. Washed platelets in a concentration of $1-2\times10^9$ platelets/ml were incubated at various temperatures in the presence of 1–20 mg/ml LYCH. Incubation temperatures and incubation times were chosen as indicated. After incubation the platelets suspensions were spun down for 20×at 14,000 RPM (table centrifuge), resuspended in buffer A, spun down for 20 s in buffer A and resuspended. Platelet counts were obtained on a Coulter counter and the samples were pelleted (centrifugation for 45 s at 14,000 RPM, table centrifuge). The pellet was lysed in 0.1% Triton buffer (10 mM TES, 50 mM KCl, pH 6.8). The fluorescence of the lysate was measured on a Perkin-Elmer LS5 spectrofluorimeter with excitation at 428 nm (SW 10 nm) and emission at 530 nm (SW 10 nm). Uptake was calculated for each sample as nanograms of LYCH per cell using a standard curve of LYCH in lysate buffer. Standard curves of LYCH, were found to be linear up to 2000 nm ml$^{-1}$.

Visualization of cell-associated lucifer yellow.

LYCH loaded platelets were viewed on a fluorescence microscope (Zeiss) employing a fluorescein filter set for fluorescence microscopy. Platelets were studied either directly after incubation or after fixation with 1% paraformaldehyde in buffer. Fixed cells were settled on poly-L-lysine coated cover slides and mounted in glycerol.

Loading of Platelets with Trehalose.

Washed platelets in a concentration of 1–2 10$^9$ platelets/ml were incubated at various temperatures in the presence of 1–20 mg/ml trehalose. Incubation temperatures were chosen from 4° C. to 37° C. Incubation times were varied from 0.5 to 4 hours. After incubation the platelet solutions were washed in buffer A two times (by centrifugation at 14,000 RPM for 20 s in a table centrifuge). Platelet counts were obtained on a coulter counter. Platelets were pelleted (45 S at 14,000 RPM) and sugars were extracted from the pellet using 80% methanol. The samples were heated for 30 minutes at 80° C. The methanol was evaporated with nitrogen, and the samples were kept dry and redissolved in H$_2$O prior to analysis. The amount of trehalose in the platelets was quantified using the anthrone reaction (Umbreit et al., *Mamometric and Biochemical Techniques*, 5$^{th}$ Edition, 1972). Samples were redissolved in 3 ml H$_2$O and 6 ml anthrone reagents (2 g anthrone dissolved in 1 l sulfuric acid). After vortex mixing, the samples were placed in a boiling water bath for 3 minutes. Then the samples were cooled on ice and the absorbance was measured at 620 nm on a Perkin Elmer spectrophotometer. The amount of platelet associated trehalose was determined using a standard curve of trehalose. Standard curves of trehalose were found to be linear from 6 to 300 µg trehalose per test tube.

Quantification of Trehalose and LYCH Concentration.

Uptake was calculated for each sample as micrograms of trehalose or LYCH per platelet. The internal trehalose concentration was calculated assuming a platelet radius of 1.2 µm and by assuming that 50% of the platelet volume is taken up by the cytosol (rest is membranes). The loading efficiency was determined from the cytosolic trehalose or LYCH concentration and the concentration in the loading buffer.

FIG. 1 shows the effect of temperature on the loading efficiency of trehalose into human platelets after a 4 hour incubation period with 50 mM external trehalose. The effect of the temperature on the trehalose uptake showed a similar trend as the LYCH uptake. The trehalose uptake is relatively low at temperatures of 22° C. and below (below 5%), but at 37° C. the loading efficiency of trehalose is 35% after 4 hours.

When the time course of trehalose uptake is studied at 37° C., a biphasic curve can be seen (FIG. 2). The trehalose uptake is initially slow (2.8×10$^{-11}$ mol/m$^2$s from 0 to 2 hours), but after 2 hours a rapid linear uptake of 3.3×10$^{-10}$ mol/m$^2$s can be observed. The loading efficiency increases up to 61% after an incubation period of 4 hours. This high loading efficiency is a strong indication that the trehalose is homogeneously distributed in the platelets rather than located in pinocytosed vesicles.

Figure 3:
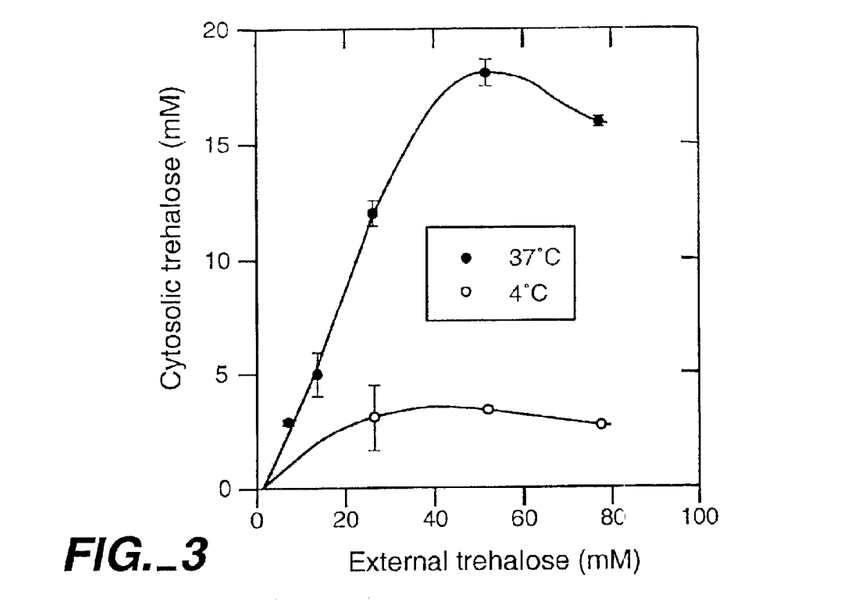
FIG. 3 graphically illustrates the internal trehalose concentration of human platelets versus external trehalose concentration as a function of time at a constant temperature of 37° C.
Figure 4:
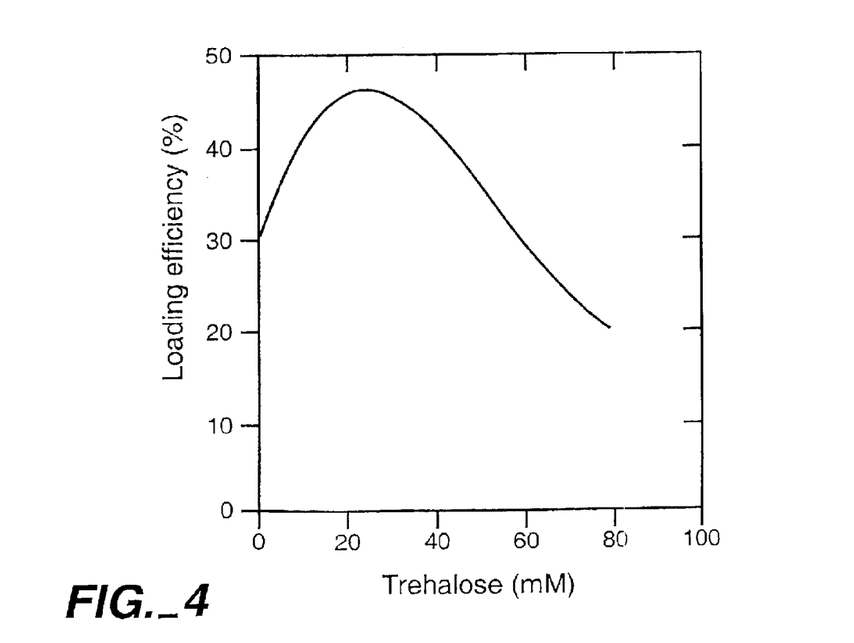
FIG. 4 graphically illustrates the loading efficiency of trehalose into human platelets as a function of external trehalose concentration.
Figure 5:
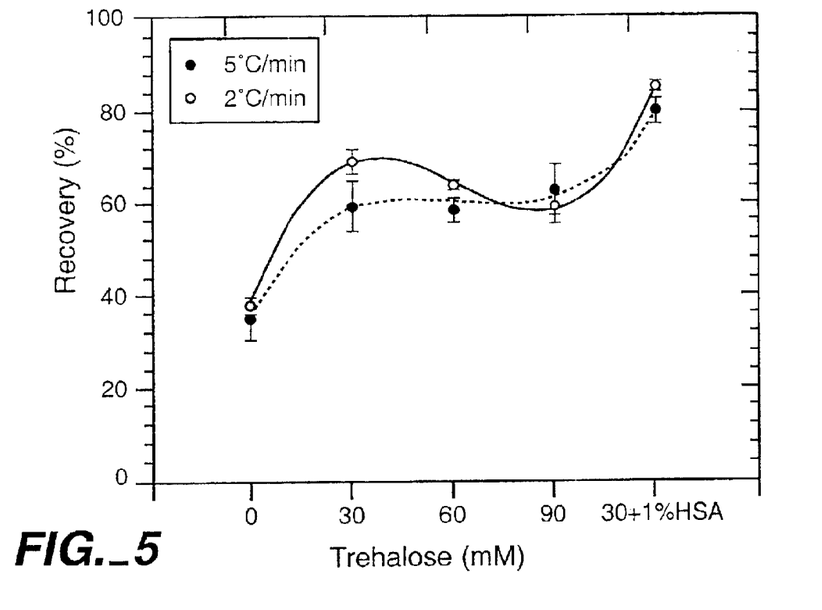
FIG. 5 graphically illustrates the recovery of platelet embodiments after lyophilization and direct rehydration with various concentrations of trehalose in the drying buffer, and in a combination of 30 mM trehalose and one percent HSA in the drying buffer.

The uptake of trehalose as a function of the external trehalose concentration is shown in FIG. 3. The uptake of trehalose is linear in the range from 0 to 30 mM external trehalose. The highest internal trehalose concentration is obtained with 50 mM external trehalose. At higher concentrations than 50 MM the internal trehalose concentration decreases again. Even when the loading buffer at these high trehalose concentrations is corrected for isotonicity by adjusting the salt concentration, the loading efficiency remains low. Platelets become swollen after 4 hours incubation in 75 mM trehalose.

The stability of the platelets during a 4 hours incubation period was studied using microscopy and flow cytometric analysis. No morphological changes were observed after 4 hours incubation of platelets at 37° C. in the presence of 25 mM external trehalose. Flow cytometric analysis of the platelets showed that the platelet population is very stable during 4 hours incubation. No signs of microvesicle formation could be observed after 4 hours incubation, as can be judged by the stable relative proportion of microvesicle gated cells (less than 3%). The formation of microvesicles is usually considered as the first sign of platelet activation (Owners et al., *Trans. Med. Rev.*, 8, 27–44, 1994). Characteristic antigens of platelet activation include: glycoprotein 53 (GP53, a lysosomal membrane marker), PECAM-1 (platelet-endothelial cell adhesion molecule-1, an alpha granule constituent), and P-selectin (an alpha granule membrane protein).

EXAMPLE 2

Washing Platelets.

Platelets were obtained from volunteers in our laboratory. Platelet rich plasma was centrifuged for 8 minutes at 320×g to remove erythrocytes and leukocytes. The supernatant was pelleted and washed two times (480×g for 22 minutes, 480×g for 15 minutes) in buffer A (100 mM NaCl, 10 mM KCl, 10 mM EGTA, 10 mM imidazole, 10 µg/ml PGE1, pH 6.8). Platelet counts were obtained on a Coulter counter T890 (Coulter, Inc., Miami, Fla.).

Loading Platelets with Trehalose.

Platelets were loaded with trehalose as described in Example 1. Washed platelets in a concentration of 1–2×10$^9$ platelets/ml were incubated at 37° C. in buffer A with 35 mM trehalose added. Incubation times were typically 4 hours. The samples were gently stirred for 1 minute every hour. After incubation the platelet solutions were pelleted (25 sec in a microfuge) and resuspended in drying buffer (9.5 mM HEPES, 142.5 mM NaCl, 4.8 mM KCl, 1 mM MgCl$_2$, 30 mM Trehalose, 1% Human Serum Albumin, 10 µg/ml PGE1). In the aggregation studies no PGE1 was added in the drying buffer. Trehalose was obtained from Pfahnstiehl. A 30% human serum albumin was obtained from Sigma.

Freezing and Drying.

Typically 0.5 ml platelet suspensions were transferred in 2 ml Nunc cryogenic vials and frozen in a Cryomed controlled freezing device. Vials were frozen from 22° C. to −40° C. with freezing rates between −30 and −1°° C./min and more often between −5 and −2° C./min. The frozen solutions were transferred to a −80° C. freezer and kept there for at least half an hour. Subsequently the frozen platelet suspensions were transferred in vacuum flasks that were attached to a Virtis lyophilizer. Immediately after the flasks were hooked up to the lyophilizer, they were placed in liquid nitrogen to keep the samples frozen until the vacuum returned to 20×10$^{-6}$ Torr, after which the samples were allowed to warm to the sublimation temperature. The condenser temperature was −45° C. Under these conditions, sample temperature during primary drying is about −40° C., as measured with a thermocouple in the sample. It is important to maintain the sample below $T_g$ for the excipient during primary drying (−32° C. for trehalose).

Rehydration. Vials with originally 0.5 ml platelet suspension were rehydrated in 1 ml PBS buffer/water (1/1). PBS buffer was composed of 9.4 mM $Na_2HPO_4$, 0.6 mM $KH_2PO_4$, 100 mM NaCl). In a few experiments PGE1 was added to the rehydration buffer in a condition of 10 μg/ml or rehydration was performed in plasma/water (1/1).

Prehydration.

Platelet lyophilisates were prehydrated in a closed box with moisture saturated air at 37° C. Prehydration times were between 0 and 3 hours.

Recovery.

The numerical recovery of lypophilized and (p)rehydrated platelets was determined by comparing the cell count with a Coulter count T890 (Coulter, Inc., Miami, Fla.) before drying and after rehydration. The morphology of the rehydrated platelets was studied using a light microscope. For this purpose platelets were fixed in 2% paraformaldehyde or gutaraldehyde and allowed to settle on poly-L-lysine coated coverslides for at least 45 minutes. After this the coverslides were mounted and inspected under the microscope. The Optical density of freeze-dried and rehydrated platelets was determined by measuring the absorbance of a platelet suspension of $1.0 \times 10^8$ cells/ml at 550 nm on a Perkin Elmer absorbance spectrophotometer.

Aggregation studies.

Dried platelets were rehydrated (after 2 hour prehydration) with 2 aliquots of platelet free plasma (plasma was centrifuged for 5 minutes at 3800×g) diluted with water in 1/1 ratio. Half ml aliquots of this platelet suspension were transferred to aggregation cuvettes with a magnetic stirrer. The response of the platelets to thrombin was tested by adding thrombin (1 U/ml) to the platelet suspension at 37° C. under stirring conditions. After 3 minutes thrombin treated platelet suspensions were inspected for clots and cell counts were done on a Coulter Counter T890.

Direct rehydration tends toward cell lysis and prehydration leads to aggregation when the cell concentration is $10^9$ cells/ml in the drying buffer. We found also that recovery of prehydrated and rehydrated platelets depends on the cell concentration in the drying buffer. The recovery drops to very low values if the cell concentration is higher than $3 \times 10^8$ cells/ml. At concentrations below $3 \times 10^8$ cells/ml, the recovery is around 70%, and no aggregates were visible. Prehydration resulted in denser cells and the absence of balloon cells.

Longer prehydration times than 90 minutes did not further improve the cellular density, but slightly activated the platelets. The water content of the pellet increases with increasing prehydration time, and preferably is between about 35% and 50% at the moment of rehydration. At higher water contents than 50% water droplets become visible in the lyophilisate (which means that the platelets are in a very hypertonic solution).

As described by Example 1, platelets were loaded with trehalose by incubation at 37° C. for 4 hours in buffer A with 35 mM trehalose, which yielded platelets with intracellular trehalose concentration of 15–25 mM. After incubation, the platelets were transferred to drying buffer with 30 mM trehalose and 1% HSA as the main excipients.

The directly rehydrated platelets had a high numerical recovery of 85%, but a considerable fraction (25–50%) of the cells was partly lysed and had the shape of a balloon. Directly rehydrated platelets were overall less dense when compared with fresh platelets.

The numerical recovery of platelets that were prehydrated in moisture saturated air was only 25% when the platelet concentration was $1 \times 10^9$ cells/ml in the drying buffer. This low recovery was due to aggregates that were formed during the prehydration period. But the cells that were not aggregated were more dense than the directly rehydrated platelets and resembled that of fresh platelets.

Since it appears desirable to dilute the platelets to prevent aggregation during the prehydration step, it may be necessary for clinical applications to concentrate the platelets following rehydration. We therefore also tested the stability of the rehydrated platelets with respect to centrifugation and found that the directly rehydrated platelets had 50% recovery after centrifugation, while the prehydrated ones had 75% recovery following centrifugation. Thus, we conclude that the inventive platelets can be concentrated without ill effect.

EXAMPLE 3

We view trehalose as the main lyoprotectant in the drying buffer. However, other components in the drying buffer, such as albumin, can improve the recovery. In the absence of external trehalose in drying buffer, the numerical recovery is only 35%. With 30 mM trehalose in the drying buffer the recovery is around 65%. A combination of 30 mM trehalose and 1% albumin gave a numerical recovery of 85%.

EXAMPLE 4

Typically 0.5 ml platelet suspensions were transferred in 2 ml Nunc cryogenic vials and frozen in a Cryomed controlled freezing device. Vials were frozen from 22° C. to −40° C. with freezing rates between −30° C./min and −1° C./min and more often between −5° C. and −2° C./min. The frozen solutions were transferred to a −80° C. freezer and kept there for at least half an hour. Subsequently the frozen platelet suspensions were transferred in vacuum flasks that were attached to a Virtus lyophilizer Immediately after the flasks were hooked up to the lyophilizer, they were placed in liquid nitrogen to keep the samples frozen until the vacuum returned to $20 \times 10^{-6}$ Torr, after which the samples were allowed to warm to the sublimation temperature. The condensor temperature was −45° C. Under these conditions, sample temperature during primary drying is about 40° C., as measured with a thermocouple in the sample. In is important to maintain the sample below $T_g$, for the excipient during primary drying (−32° C. for trehalose). Only minor differences in recovery were found as a function of the freezing rate. The optimal freezing rate was found to be between 2° C. and 5° C./minute.

EXAMPLE 5

Response of freeze-dried platelets to thrombin (1 U/mi) was compared with that of fresh platelets. The platelet concentration was $0.5 \times 10^8$ cells/ml in both samples. 500 μl platelets solution was transferred into aggregation vials. Thrombin was added to the samples and the samples were stirred for 3 minutes at 37° C. The cell counts that were determined after 3 minutes were 0 for both the fresh and the freeze-dried platelets. The response to thrombin was determined by a cleavage in glycoprotein 1b-(GP1b). This was detected by using monoclonal antibodies and flow cytometry. Thus, the pattern seen after addition of thrombin was a reduced amount of GP1b on the platelet surface.

The response of lyophilized, prehydrated, and rehydrated platelets (Examples 1 and 2) to thrombin (1 U/ml) was found to be identical compared with that of fresh platelets. In both fresh and rehydrated platelets a clot was formed within 3 minutes at 37° C. These clots are illustrated by FIG. 8, panels (A) and (B). When cell counts were done with the Coulter counter, we found no cells present, indicating that all platelets participated in forming the clot illustrated in panel (B).

EXAMPLE 6

Reactions with other agonists were studied. Platelet suspensions of the inventive platelets were prepared with $50 \times 10^6$ platelets/ml. Different agonists were then added and subsequently counted with a Coulter counter to determine the percentage of platelets involved in the visually observable clot formation. The cell count was between 0 and $2 \times 10^6$ platelets/ml:

after 5 minutes with 2 mg/ml collagen
after 5 minutes with 20 μM ADP
after 5 minutes with 1.5 mg/ml ristocetin This means that the percentage of platelets that are involved in clot formation is between 95–100% for all the agonists tested. The agonist concentrations that were used are all physiological. In all cases the percentage of clotted platelets was the same as fresh control platelets.

It is to be understood that while the invention has been described above in conjunction with preferred specific embodiments, the description and examples are intended to illustrate and not limit the scope of the invention, which is defined by the scope of the appended claims.

It is claimed:

1. A process of preparing a dehydrated composition comprising:
   providing platelets selected from a mammalian species, the platelets being effectively loaded by fluid phase endocytosis with an oligosaccharide therein to preserve biological properties, wherein the loading includes incubating the platelets at a temperature from about 30° C. to less than about 40° C. with an oligosaccharide solution, the solution having up to about 50 mM oligosaccharide therein, the incubating sufficient to load oligosaccharide inside the platelets in an amount from about 10 mM to about 50 mM;
   cooling the loaded platelets to below their freezing point; and
   lyophilizing the cooled platelets.

2. The process as in claim 1 wherein the platelets are human platelets.

3. The process as in claim 1 wherein the incubating temperature is about 37° C.

4. The process as in claim 1 wherein the incubating is for at least about two hours.

5. The process as in claim 1 wherein the incubating is for at least about four hours.

6. The process as in claim 1 wherein the platelets are human platelets, the incubating is between about 30° C. and about 37° C., the solution has trehalose in an amount between about 20 mM and 50 mM, and the incubation is for at least about four hours.

7. The process as in claim 6 wherein the cooling is at a rate of about 2° C. to 5° C. per minute and is conducted in a drying buffer.

8. The process as in claim 1 wherein the lyophilizing is conducted at a temperature below about −32° C. and removes about 95 weight percent of water.

9. The process of claim 1 additionally comprising placing the platelets in a resting state prior to cooling.

10. The process of claim 1 additionally comprising preventing the loaded platelets from activating prior to cooling.

11. The process of claim 1 wherein said loading with an oligosaccharide includes increasing a loading efficiency of the oligosaccharide into the platelets by maintaining a concentration of the oligosaccharide in the oligosaccharide solution at less than about 50 mM.

12. The process of claim 1 wherein said loading with an oligosaccharide includes loading with a loading efficiency ranging from about 45% to about 50% for the oligosaccharide solution having an oligosaccharide concentration ranging from about 20 mM to about 30 mM.

13. The process of claim 1 wherein said oligosaccharide comprises trehalose.

14. The process of claim 11 wherein said oligosaccharide comprises trehalose.

15. The process of claim 12 wherein said oligosaccharide comprises trehalose.

16. The process of claim 1 wherein said loading with an oligosaccharide includes decreasing a loading efficiency of the oligosaccharide into the platelets by providing a concentration of the oligosaccharide in the oligosaccharide solution at greater than about 50 mM.

17. The process of claim 16 herein said oligosaccharide comprises trehalose.

18. The process of claim 1 wherein said loading is without a fixative.

19. The process of claim 1 additionally comprising prehydrating the lyophilized cooled platelets.

20. The process of claim 19 wherein said prehydrating comprises exposing the lyophilized cooled platelets to moisture saturated air.

21. The process of claim 1 additionally comprising prehydrating the lyophilized cooled platelets until the water content of the lyophilized cooled platelets ranges from about 35% by weight to about 50% by weight.

22. The process of claim 19 additionally comprising rehydrating the prehydrated lyophilized cooled platelets.

23. A process for preparing a dehydrated composition comprising:
   loading internally by fluid phase endocytosis platelets with a protectorate to produce internally loaded platelets; preventing the internally loaded platelets from activating; cooling the internally loaded platelets to below their freezing point; and lyophilizing the cooled internally loaded platelets.

24. The process of claim 23 wherein said preventing comprises placing the internally loaded platelets in a resting state.

25. The process of claim 23 wherein said protectorate comprises an oligosaccharide.

26. The process of claim 9 wherein said placing the platelets in a resting state comprises employing a channel blocking agent.

27. A process for preparing a dehydrated composition comprising:
   loading internally by fluid phase endocytosis platelets with from about 10 mM to about 50 mM oligosaccharide to produce internally loaded platelets; cooling the internally loaded platelets to below their freezing point; and lyophilizing the cooled internally loaded platelets.

28. The process of claim 27 additionally comprising drying the internally loaded platelets prior to said cooling.

29. The process of claim 28 wherein said drying comprises suspending the internally loaded platelets in a drying solution containing a water replacing molecule.

30. The process of claim 29 wherein said drying solution comprises up to about 100 mM of an oligosaccharide.

31. The process of claim 27 wherein said cooling comprises cooling the internally loaded platelets to a temperature below about −32° C.

32. The process of claim 27 wherein said loading comprises incubating platelets at a temperature greater than about 25° C.

33. The process of claim 27 wherein said loading is without a fixative.

34. The process of claim 27 wherein said loading with an oligosaccharide includes increasing a loading efficiency of the oligosaccharide into the platelets by maintaining a concentration of the oligosaccharide in the oligosaccharide solution at less than about 50 mM.

35. The process of claim 27 wherein said loading with an oligosaccharide includes loading with a loading efficiency ranging from about 45% to about 50% for the oligosaccharide solution having an oligosaccharide concentration ranging from about 20 mM to about 30 mM.

36. The process of claim 27 wherein said oligosaccharide comprises trehalose.

37. The process of claim 34 wherein said oligosaccharide comprises trehalose.

38. The process of claim 35 wherein said oligosaccharide comprises trehalose.

39. The process of claim 27 wherein said loading with an oligosaccharide includes decreasing a loading efficiency of the oligosaccharide into the platelets by providing a concentration of the oligosaccharide in the oligosaccharide solution at greater than about 50 mM.

40. The process of claim 39 herein said oligosaccharide comprises trehalose.

41. The process of claim 27 wherein said loading is without a fixative.

42. The process of claim 27 additionally comprising prehydrating the lyophilized cooled platelets.

43. The process of claim 42 wherein said prehydrating comprises exposing the lyophilized cooled platelets to moisture saturated air.

44. The process of claim 27 additionally comprising prehydrating the lyophilized cooled platelets until the water content of the lyophilized cooled platelets ranges from about 35% by weight to about 50% by weight.

45. The process of claim 42 additionally comprising rehydrating the prehydrated lyophilized cooled platelets.

* * * * *